United States Patent
Alver et al.

(10) Patent No.: US 9,691,144 B2
(45) Date of Patent: Jun. 27, 2017

(54) SYSTEM AND METHOD FOR COUNTING ZOOPLANKTON

(71) Applicant: SINVENT AS, Trondheim (NO)

(72) Inventors: Morten Alver, Trondheim (NO); Yngve Attramadal, Trondheim (NO)

(73) Assignee: C-FEED AS, Trondheim (NO)

(*) Notice: Subject to any disclaimer, the term of this patent is extended or adjusted under 35 U.S.C. 154(b) by 0 days.

(21) Appl. No.: 14/762,990

(22) PCT Filed: Jan. 27, 2014

(86) PCT No.: PCT/NO2014/050015
§ 371 (c)(1),
(2) Date: Jul. 23, 2015

(87) PCT Pub. No.: WO2014/116120
PCT Pub. Date: Jul. 31, 2014

(65) Prior Publication Data
US 2015/0356725 A1 Dec. 10, 2015

(30) Foreign Application Priority Data
Jan. 28, 2013 (NO) .................................. 20130147

(51) Int. Cl.
*G06K 9/00* (2006.01)
*G06T 7/00* (2017.01)
(Continued)

(52) U.S. Cl.
CPC ....... *G06T 7/0004* (2013.01); *G01N 15/1463* (2013.01); *G06M 1/101* (2013.01);
(Continued)

(58) Field of Classification Search
CPC ............... G06T 7/0004; G06T 5/003; G06T 2207/20021; G06T 2207/30242;
(Continued)

(56) References Cited

U.S. PATENT DOCUMENTS 4,637,719 A * 1/1987 Herman ............. G01N 15/1429
356/442
6,141,097 A 10/2000 Herman
(Continued)

FOREIGN PATENT DOCUMENTS

EP 2 455 914 B1 10/2012
GB 1 300 585 12/1972
(Continued)

OTHER PUBLICATIONS

Cabell S. Davis et al., "Real-time observation of taxa-specific plankton distributions: an optical sampling method", Marine Ecology Progress Series, vol. 284, Dec. 1, 2004, pp. 77-96, XP055121848.*
(Continued)

*Primary Examiner* — Andrew Moyer
(74) *Attorney, Agent, or Firm* — Wenderoth, Lind & Ponack, L.L.P.

(57) ABSTRACT

A method and a system for density measurement of zooplankton in situ in an aqueous solution are provided. The method comprises acquiring at least one image of a volume of the aqueous solution; processing the at least one image and identifying particles in the at least one image; analyzing the identified particles based on a sharpness of each particle, and identifying zooplankton to be counted.

15 Claims, 8 Drawing Sheets

(51) Int. Cl.
*G06T 5/00* (2006.01)
*G06M 11/00* (2006.01)
*G06M 1/10* (2006.01)
*G01N 15/14* (2006.01)
*G01N 15/00* (2006.01)

(52) U.S. Cl.
CPC .............. *G06M 11/00* (2013.01); *G06T 5/003* (2013.01); *G01N 2015/0053* (2013.01); *G01N 2015/0065* (2013.01); *G01N 2015/1447* (2013.01); *G01N 2015/1452* (2013.01); *G01N 2015/1486* (2013.01); *G06T 2207/20021* (2013.01); *G06T 2207/20036* (2013.01); *G06T 2207/30128* (2013.01); *G06T 2207/30242* (2013.01)

(58) Field of Classification Search
CPC ........... G06T 2207/30128; G06T 2207/20036; G06M 1/101; G06M 11/00; G01N 15/1463; G01N 2015/1447; G01N 2015/0053; G01N 2015/1452
USPC ........................................................ 382/100
See application file for complete search history.

(56) References Cited

U.S. PATENT DOCUMENTS

2012/0137574 A1* 6/2012 Stephen ................ A01K 61/00
44/388

2013/0266215 A1* 10/2013 Brookhart ................ G06K 9/00
382/162

FOREIGN PATENT DOCUMENTS

| JP | 2011-223924 | 11/2011 |
| WO | 2010/104908 | 9/2010 |

OTHER PUBLICATIONS

International Search Report issued Jun. 16, 2014 in corresponding International Application No. PCT/NO2014/050015.
International Preliminary Report on Patentability issued Feb. 23, 2015 in corresponding International Application No. PCT/NO2014/050015.
Norwegian Search Report issued May 13, 2013 in corresponding Norwegian Application No. 20130147.
Cabell S. Davis et al., "A three-axis fast-tow digital Video Plankton Recorder for rapid surveys of plankton taxa and hydrography", Limnology and Oceanography: Methods, vol. 3, Jan. 1, 2005, pp. 59-74, XP055121589.
C. S. Davis et al., "The Video Plankton Recorder (VPR): Design and Initial results", Archiv Fur Hydrobiologie, Beihefte, Ergebnisse Der Limnologie, vol. 36, Jul. 1, 1992, pp. 67-81, XP055121598.
Jules S. Jaffe et al., "Underwater Optical Imaging: Status and Prospects", Oceanography, vol. 14, No. 3, Jan. 1, 2001, pp. 64-75, XP055093781.
Morten Omholt Alver et al., "Automatic measurement of rotifer *Brachionus plicatilis* densities in first feeding tanks", Aquacultural Engineering 36, 2007, pp. 115-121.

* cited by examiner

SYSTEM AND METHOD FOR COUNTING ZOOPLANKTON

BACKGROUND OF THE INVENTION

1. Field of the Invention

The present invention concerns an apparatus and a method for counting zooplankton in a liquid medium, and in particular copepods in an aqueous medium.

2. Description of Related Art

It is well known that copepods are a sort of "vitamin bomb" for fish fry. Copepods are a type of zooplankton and the nutritional value is regarded as being better than that of rotifers. The aim is to produce copepod eggs that may be harvested and purified for further sale. When used as feed to fish, the eggs are cultured and hatched, and the resulting copepods are used to feed the fish. Copepods may be used as feed for marine fish larvae in, e.g., an aquaculture facility or aquarium. Also, good results have been achieved with copepod eggs as a start-feed for the offspring of rare aquarium fish. The copepods may be of the type *Acartia tonsa*.

In a large production plant for copepods for production of copepod eggs, it is desirable to provide an automated process for the egg production. Manual counting of copepod densities is time consuming, and for this reason and others, the production of live food amounts to a significant part of the production costs for marine fish species. Today's copepod plants require a human operator presence in order to distribute feed in accordance with growth and density of copepods. To enable better monitoring of copepod cultures and feed densities in larval tanks, a more efficient measurement method is needed. By exploiting the fact that copepods can be visually distinguished in size and shape from other particles present in culture water, the counting process can be automated.

An automated process for counting rotifers in culture water is schematically illustrated in FIG. 1 and described in M. O. ALVER et al.: "Automatic measurement of rotifer Brachionus plicatilis densities in first feeding tanks"; Aquacultural Engineering 36 (2007) 115-121. An imaging box 1 is provided with an object glass 2 inside. Computer controlled pumps 3 and valves 4 make it possible to automatically extract samples from one or several feeding tanks 5 into the object glass 2 inside the imaging box 1. The object glass 2 provides a defined volume at a distance from a digital camera 6. The defined volume is provided by a space between the two glass plates constituting the object glass 2. The space between the two glass plates can be chosen depending on the desired sample volume, and the focus depth of the camera. For high densities, a shorter space should be chosen to reduce the risk of rotifers overlapping in the picture. The rotifers in the volume are photographed by the digital camera and the digital image processed by image processing to obtain a rotifer density inside the fixed volume. FIG. 2 shows an arrangement of light sources 7, object glass 2 and camera lens 6 of the prior art rotifer counter shown in FIG. 1. Lighting is provided by 16 light emitting diodes 7 mounted in a square with four diodes along each side. The square is arranged so the cone visible to the camera (camera line of sight) falls in between the light emitting diodes 7. This set-up provides dark field conditions, where light is reflected by particles in the water, causing rotifers and other particles to appear in the images as bright spots against a dark background. Dark field conditions provide images with better contrast than bright field conditions.

The principles of the rotifer counter can be used for organisms that move sufficiently slowly or do not respond strongly to stimuli such as pumping or light. However, organisms such as copepodites of Acartia, and many other species, move rapidly, react to pressure gradients caused by pumping, and show strong taxis toward light. When pumping samples from a tank, this behavior invalidates the assumption that the plankton density in the measurement volume equals the density in the tank.

SUMMARY OF THE INVENTION

The invention provides a solution to the problems identified above.

In a first aspect, the invention provides a method for density measurement of zooplankton in situ in an aqueous solution, the method comprising:
acquiring at least one image of a volume V of the aqueous solution;
processing the at least one image and identifying particles in the at least one image;
analyzing the identified particles based on a sharpness of each particle, and
identifying zooplankton to be counted.

Analyzing a sharpness of each particle may comprise tracing a boundary of each identified particle. Further, analyzing a sharpness of each particle may also comprise calculating an intensity gradient for each pixel along the boundary of each particle from the at least one image based on a rate of change of intensity between neighboring pixels, and calculating a mean intensity gradient of all the pixels along the boundary of each particle. Analyzing a sharpness of each particle may further comprise correcting the mean intensity gradient for a general contrast level in the at least one image.

The method may further comprise filtering of the identified particles in the at least one image based on shape parameters identifying which particles are zooplankton to be counted. An illumination device for illumination of the volume of the aqueous solution may be controlled in interaction with image acquiring and processing.

In a second aspect, the invention provides a system for density measurement of zooplankton in situ in an aqueous solution, comprising an imaging device for acquiring at least one image of a volume V of the aqueous solution; a plate arranged at a distance from the imaging device, the distance and a view angle of the imaging device defining the volume V of the aqueous solution imaged by the imaging device; and an image processing device performing image processing of the at least one image from the imaging device identifying particles in the image, analyzing the identified particles based on a sharpness of each particle, and identifying zooplankton to be counted.

In a further embodiment, the imaging device may comprise a camera housing including at least one digital camera. At least one illuminating device is provided illuminating the volume of the aqueous solution. A controller may be provided for controlling the imaging device and the illuminating device based on feedback from the image processing device.

In further aspects, the invention provides use of the system and method above for establishing a density of zooplankton copepods in an aqueous solution. The system and method may also be used for controlling the distribution of food to copepods in an automated zooplankton egg production facility. The zooplankton may be copepods.

In a further aspect, the invention also provides a computer program adapted to be executed in a computer comprising a processor and a readable storage medium, for performing the method above. In an even further aspect, the invention provides a computer program product having stored thereon instructions for performing the method as defined above.

With the present invention, the number of zooplankton is counted in situ in the aqueous solution. The zooplankton are not disturbed by pumping, currents induced in the solution or strong light. This provides a simple and reliable measurement without disturbing or harming the zooplankton to be measured. The measurement does not rely on moving parts or tubes and object glasses that need replacement, and can be produced at a low cost.

BRIEF DESCRIPTION OF THE DRAWINGS

Example embodiments of the invention will now be described with reference to the followings drawings, where.

DETAILED DESCRIPTION

Figure 1:
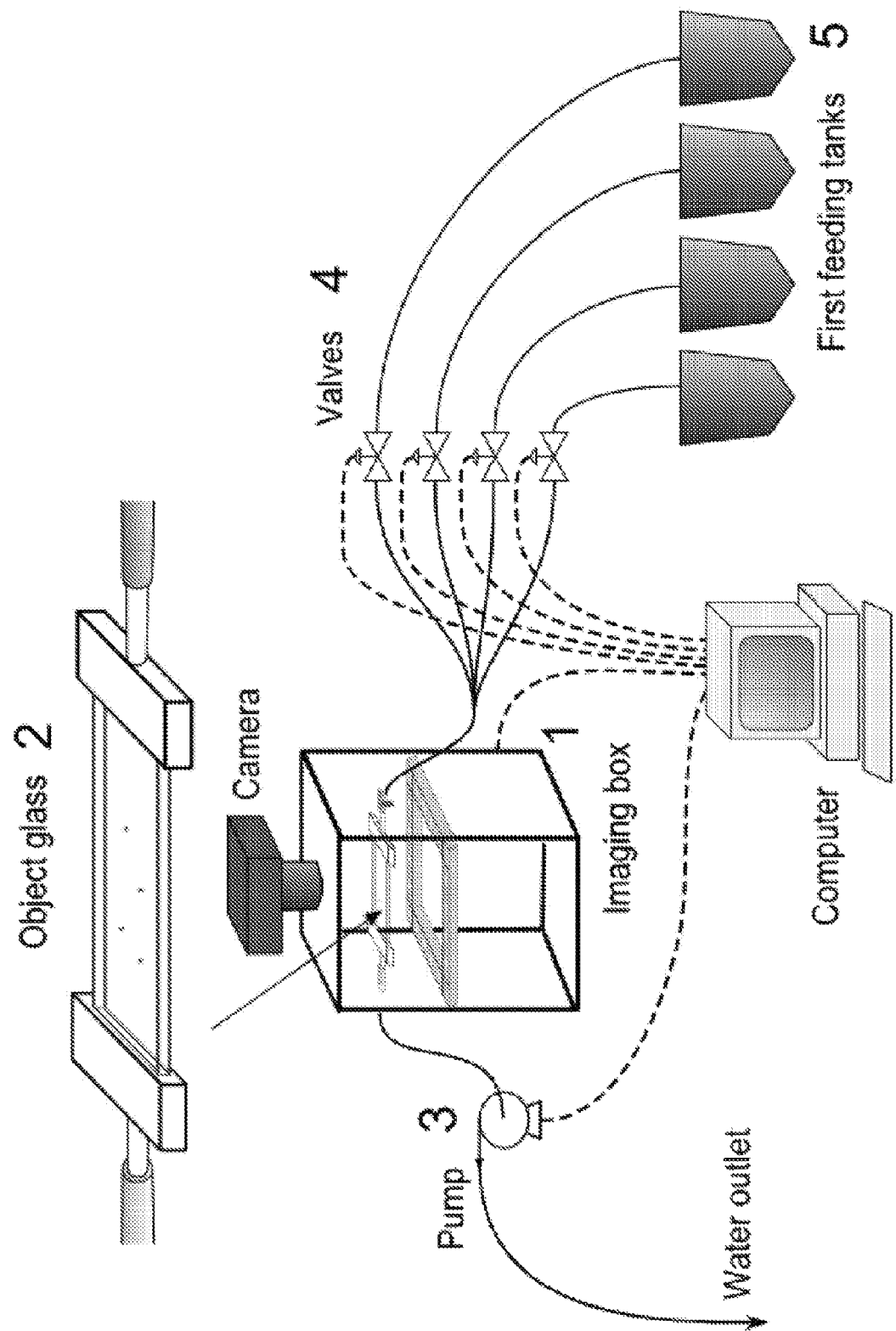
FIG. 1 shows an overview of a rotifer counter according to prior art.
Figure 2:
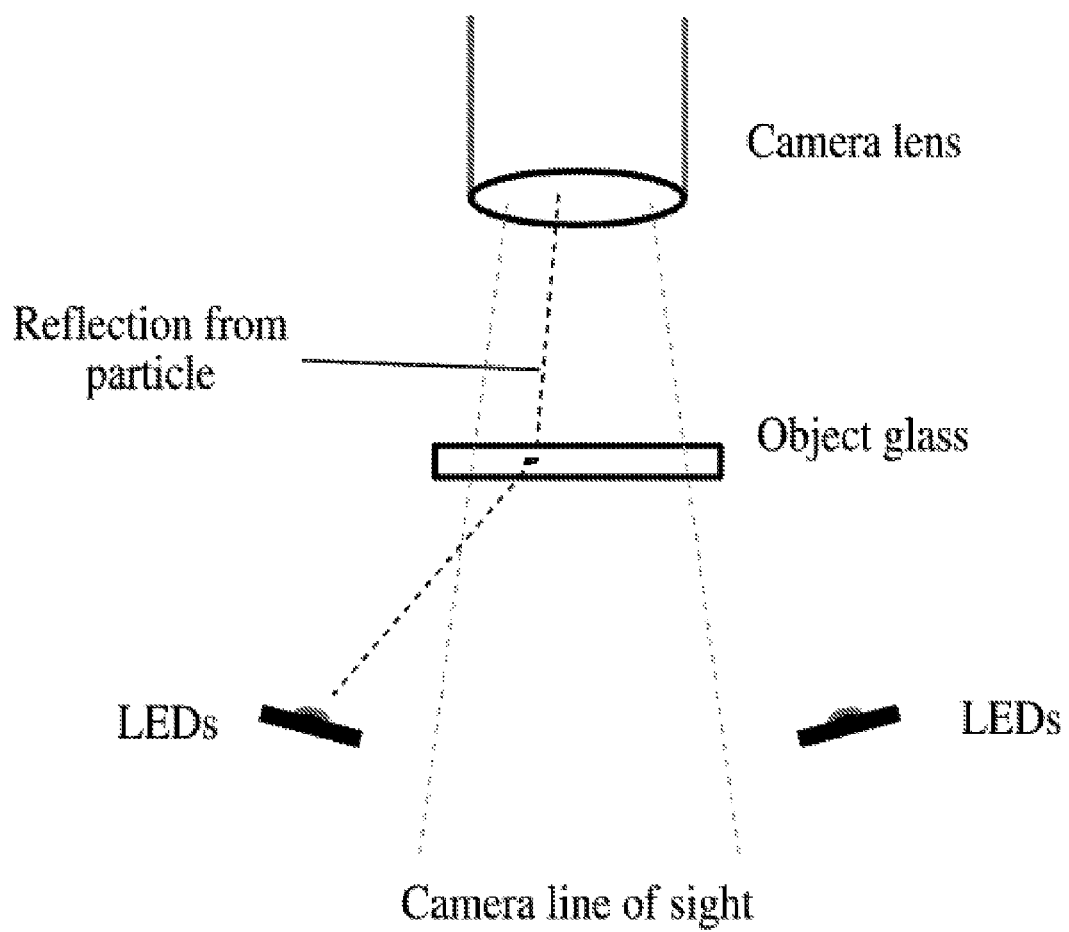
FIG. 2 shows an arrangement of light sources, an object glass and a camera lens of the prior art rotifer counter shown in FIG. 1.
Figure 3A:
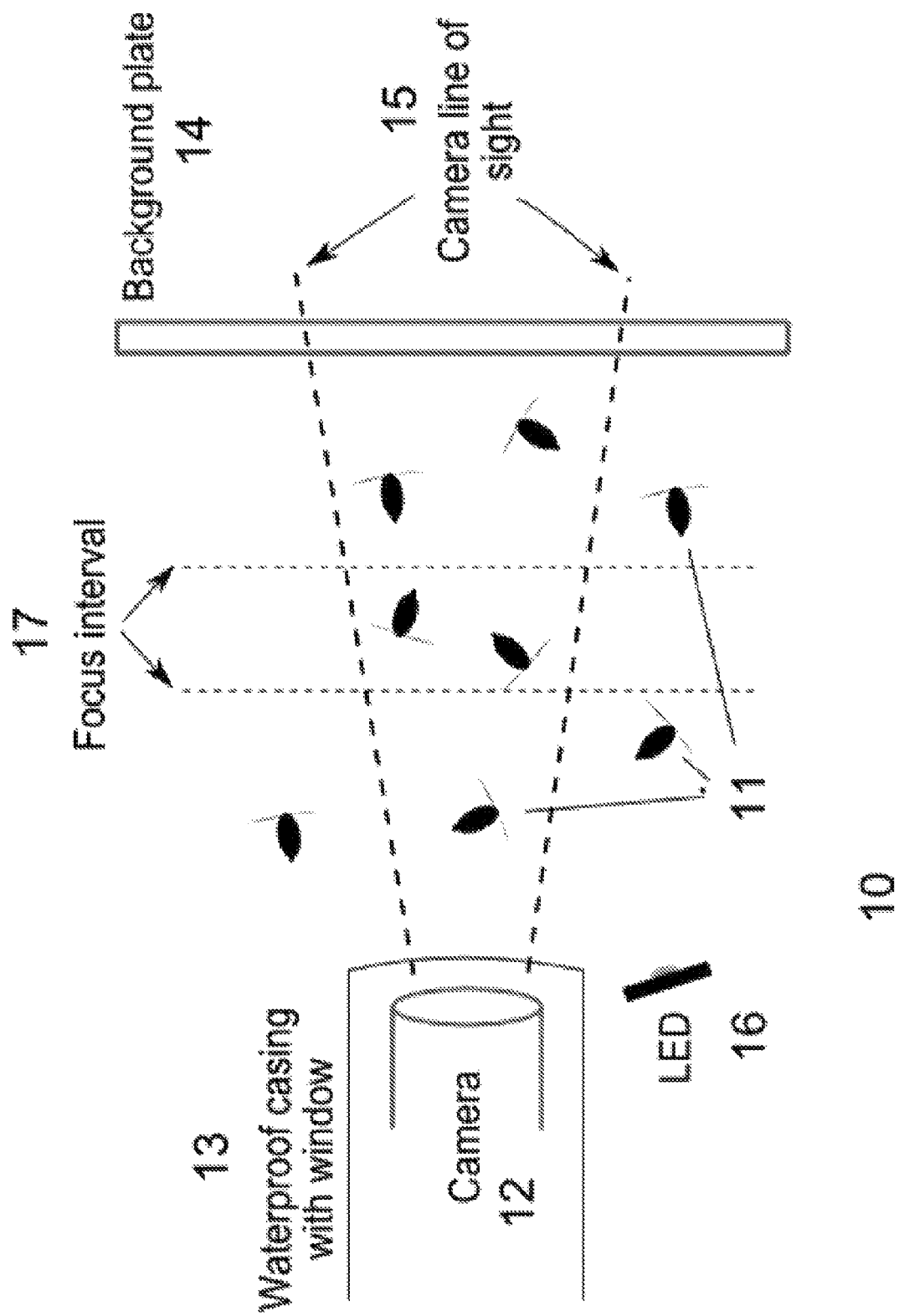
FIG. 3a and FIG. 3b show a schematic view of a counter for zooplankton according to an embodiment of the invention.
Figure 3B:
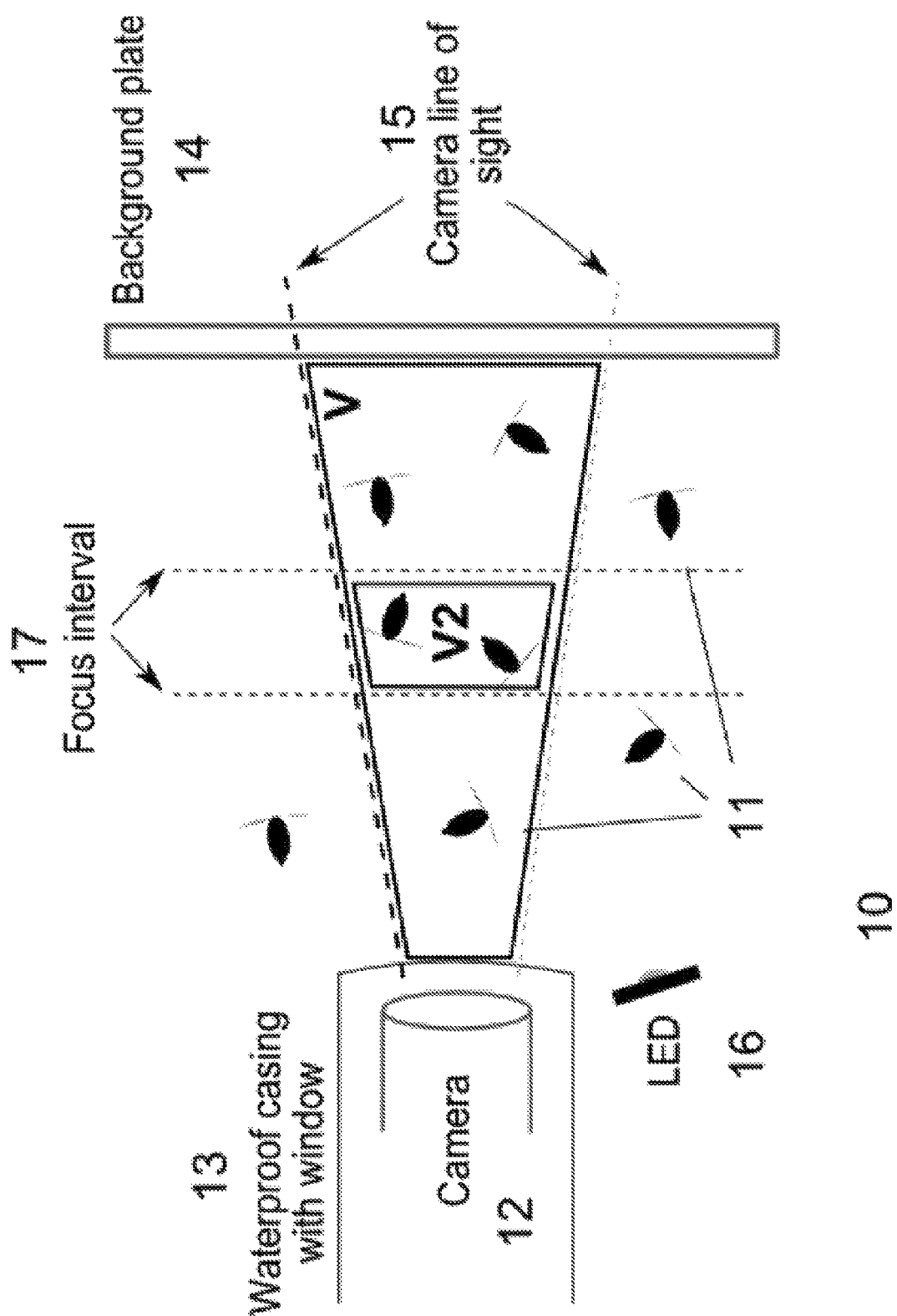

FIG. 3a shows an in situ counter 10 for zooplankton 11 in an aqueous solution. An imaging device in the form of a camera 12 is arranged in a waterproof camera housing 13. The camera housing is provided with a window for the camera. The camera is preferably a digital camera providing a digital image with pixels, but other digital imaging devices may be envisaged. A background plate 14 is provided in front of the camera 12 parallel with the camera lens 21. The camera line of sight 15 falls within the area defined by the background plate 14. The background plate 14 may be attached to an arm (not shown in FIG. 3a) connected to the camera housing 13. The background plate 14 is white to obtain a good contrast for the zooplankton 11 to be photographed. As shown in FIG. 3b, the view angle (camera line of sight) of the camera lens 21 and the distance between the camera lens and the background plate 14 define a volume, V, photographed by the camera. Within the volume V, there is a smaller volume, $V_2$, limited by a focus interval 17 of the camera lens 21, where particles in the water are captured sharply. The volume $V_2$ is thus delimited in two dimensions by the field of view of the camera, and in the third dimension by the focus interval 17.

Only particles within this focus interval 17 will become sharp in the image. An image acquired by the camera is processed by an image processing device and particles in the image identified. The identified particles are analyzed based on a sharpness of each particle, and zooplankton to be counted identified. As the volume $V_2$ is known, a density may be obtained.

A light source 16 is provided on a side of the camera illuminating the volume V to be photographed. The light source 16 preferably provides white light and may be a light emitting diode (LED) or another suitable light source. The light source may be attached to the camera housing 13 or the arm connected to the camera housing. In a further embodiment, the camera housing may be provided with two light sources arranged on each side of the camera. This enables a more even and stronger illumination and provides a stronger contrast between the white plate background and the zooplankton in the volume to be photographed.

Figure 3C:
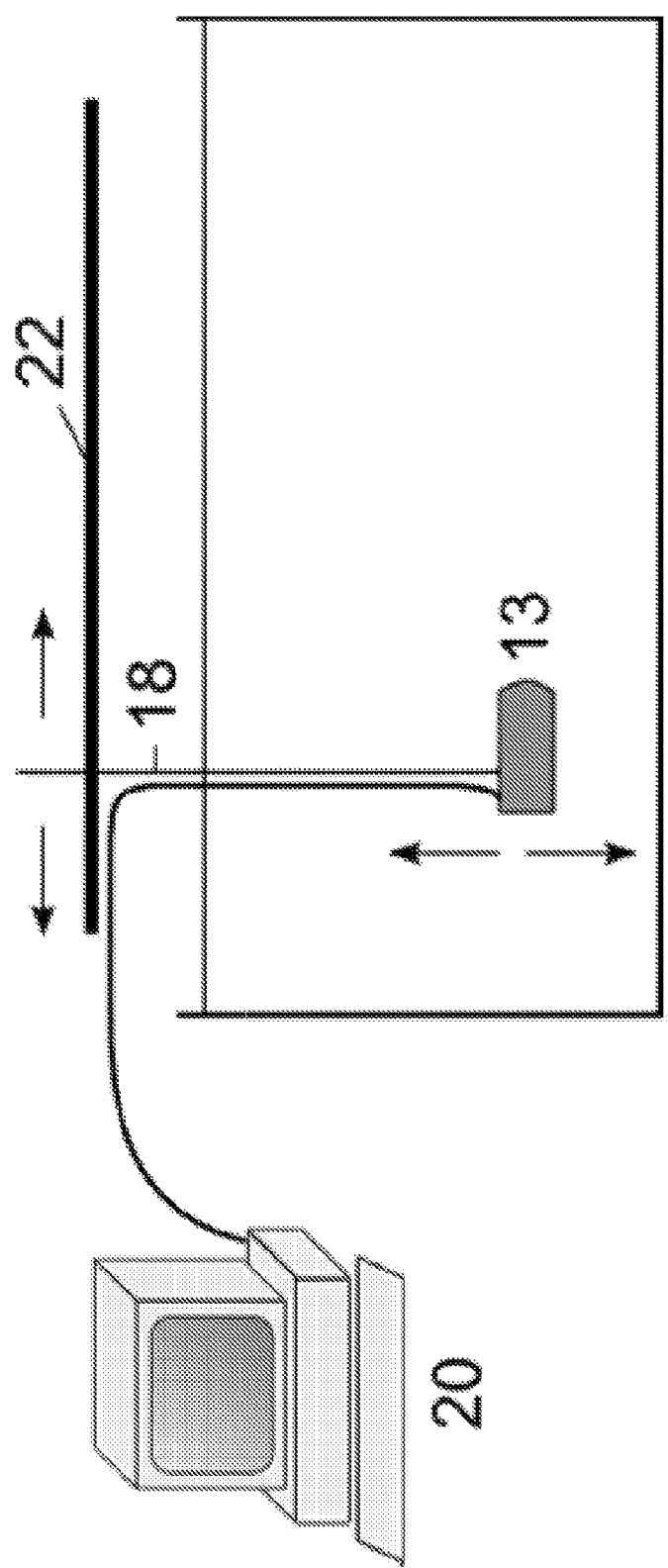
FIG. 3c shows a schematic view of a system for counting zooplankton according to an embodiment of the invention, where the counter for zooplankton is submerged in an aqueous solution.

The camera housing 13 with distance arm and background plate is adapted to be submerged into the tank 19 containing the aqueous solution with zooplankton to be monitored as shown in FIG. 3c. The camera housing 13 may also be arranged, e.g., on a pole 18 in order to be arranged in different positions inside the tank. The pole may be connected to a motorized arrangement. FIG. 3c shows an embodiment with a camera housing 13 on a pole 18. The pole may be moved in all directions for positioning anywhere inside the tank. The arrows in FIG. 3c only indicate movement in two directions for simplicity of the drawing, but movements in the other directions are also possible. The camera housing 13 may move up and down in the pole. The camera 12 inside the camera housing 13 is connected to a computer 20 for analyzing the images, and controlling the camera, light sources and the motorized arrangement. A controller, exemplified by a computer in FIG. 3c, controls the imaging device and the illuminating device based on feedback from the image processing device.

The camera is connected to a control device with software for counting zooplankton. The control device may be a standard computer with a control interface. The software is provided with an image processing algorithm according to the invention, which will be explained in further detail below. The light source is driven by a light module. The light module is connected to the control device. The control module also comprises a light control interface controlling the light source. The control interfaces for the light source and the camera are coordinated by the software implementing the image processing algorithm. The light source preferably only provides light in short periods when a new picture is to be taken in order to minimize the effect on the behavior of the zooplankton.

The camera of the in-situ counter acquires a number of images of the volume V inside the aqueous solution with zooplankton. One image may be sufficient for counting the number of zooplankton at a given time, but normally a number of consecutive images are acquired and analyzed in order to provide a more accurate estimate of the density of zooplankton in the aqueous solution at a given time. If a number of consecutive images are acquired, each image is processed separately, and then an average of the number of zooplankton is estimated. The at least one image is processed by the image processing algorithm and the particles in the image identified. The identified particles are further analyzed with regard to a sharpness of each particle, and the zooplankton to be counted identified. Analyzing with respect to a sharpness of each particle enables filtering out of particles outside the focus interval of the camera lens, thereby providing counting of zooplankton within the defined volume $V_2$.

The image processing algorithm may provide the following steps:

Analyzing a sharpness of each particle may include tracing a boundary of each identified particle. An intensity gradient for each pixel along the boundary of each particle may be calculated from the at least one image based on a rate of change of intensity between neighboring pixels, and by calculating a mean intensity gradient of all the pixels along the boundary of each particle. The identified particles in the at least one image may be filtered based on shape parameters identifying which particles are zooplankton to be counted.

Further details of the steps of the image processing algorithm are provided below.

1. Smoothing of intensity. The image is split into a number of (n×m) parts; e.g., 5×5 parts. The average (mean or median) intensity is calculated for the pixels in each part, and then adjusted up or down for each part based on a deviation from a mean of the average intensities for the number of parts (n×m) (e.g., 5×5 parts). The adjustment is interpolated in each pixel to avoid sharp gradients on the borders between the parts.
2. Smoothing of the image to remove high frequency variations.
3. Thresholding of the image to provide a binary image. Thresholding of the image is performed at an intensity level in between an average intensity level of the image and the darkest pixel in the image, at a minimum distance from the average intensity level. The weighting of the average intensity level compared to the darkest level (darkest pixel) to find the threshold level is adjustable depending on the lighting of the volume photographed by the camera and the zooplankton to be measured. The resulting binary image is reversed so pixels darker than the threshold level become white, and the remaining pixels black.
4. Erosion of the reversed binary image to remove small particles (particles covering only a small number of pixels, typically 1-10 pixels in this context). Removing these small particles reduces the calculation time for the further image processing of the image.
5. The particles in the reversed binary image, which are collections of connected white pixels, are then filtered by size. Particles along the image edges are discarded, and the remaining particles are analyzed with regard to sharpness. Analyzing with regard to sharpness is done by first tracing the boundary of each particle. For each pixel along the boundary of a particle, the intensity gradient is calculated from the original image; i.e., the acquired image before the start of imaging processing in step 1) based on the rate of change of intensity between the neighboring pixels. The sharpness of the particle is defined as the mean gradient of all the pixels along the boundary of the particle, corrected for a general contrast level in the original image. All particles with sharpness below a certain level are discarded. This represents a filtering out of particles outside the focus interval of the camera lens.
6. The remaining particles after filtering based on sharpness may be further filtered using well-known shape parameters such as circularity factor, elongation, moments of inertia, convex area and compactness to decide which particles are of the zooplankton species to be counted, and which are detritus or other organisms.

The image processing algorithm described above results in a number of identified particles to be counted. All these identified particles are then measured in the processed image with regard to size in pixels, and this size in pixels may then be converted to an approximate volume estimate for each zooplankton.

The principle can potentially be used on a wide range of planktonic organisms, including fish larvae.

Examples

The counter was tested in an aquarium with first a high density of copepods, and then a low density of copepods. Bubbling of the aquarium was provided in order to create calm circulation in the aquarium. The counter was set to store about 500 images an hour for each density, with approximately 7 seconds between each image.

Figure 4:
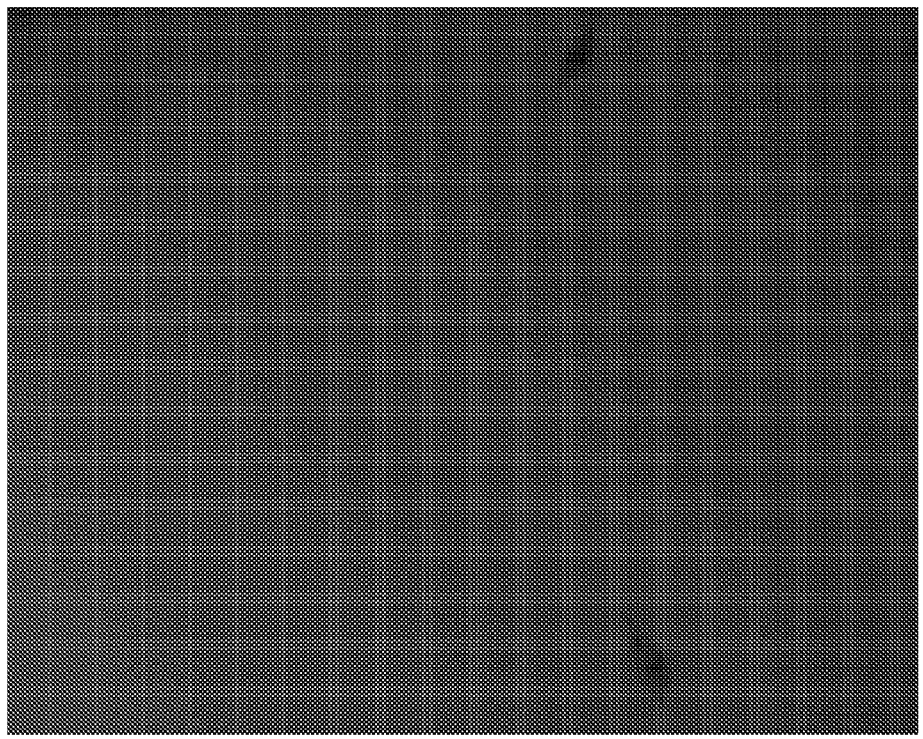
FIG. 4 shows an example of use of the counter according to an embodiment of the invention for counting *Acartia tonsa* showing an image where two individuals are in focus.
Figure 5:
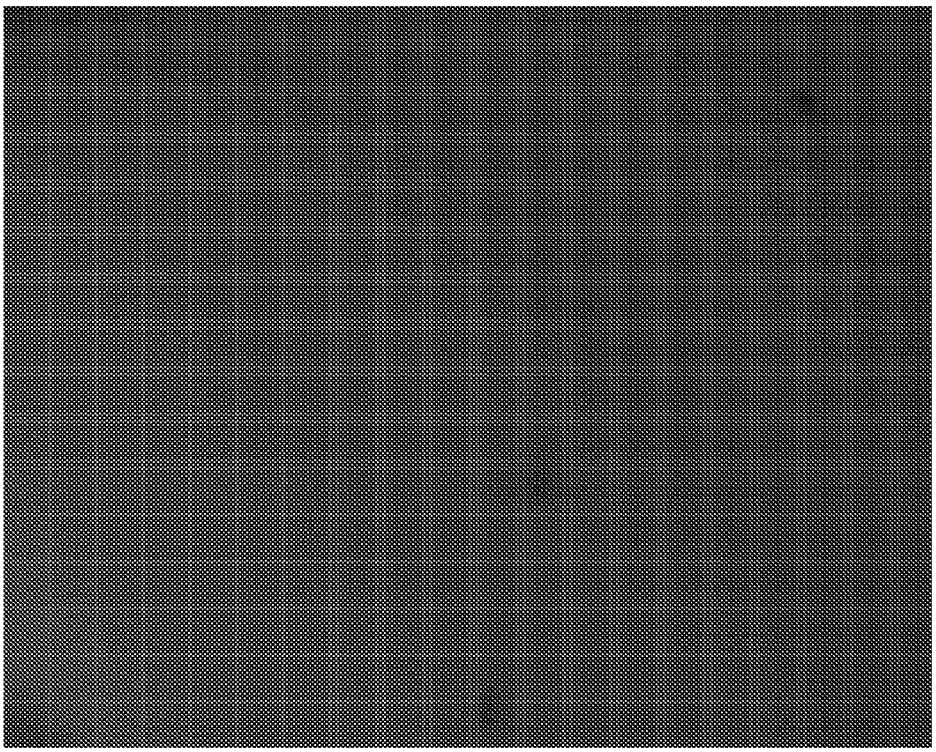
FIG. 5 shows an example of use of the counter according to an embodiment of the invention for counting *Acartia tonsa* showing an image of a number of individuals in different degrees of focus.

FIG. 4 shows an example of an image after image processing based on sharpness with two copepods in focus. FIG. 5 shows the result after image processing based on sharpness with individual copepods in different degrees of focus. Only the copepods of sufficient sharpness are counted, the remaining copepods are filtered out. In FIG. 5 only one of the copepods, the one in the upper corner, is sharp enough to be counted. The threshold for sufficient sharpness is set in advance for the camera and lighting setup based on visual inspection of images.

Figure 6:
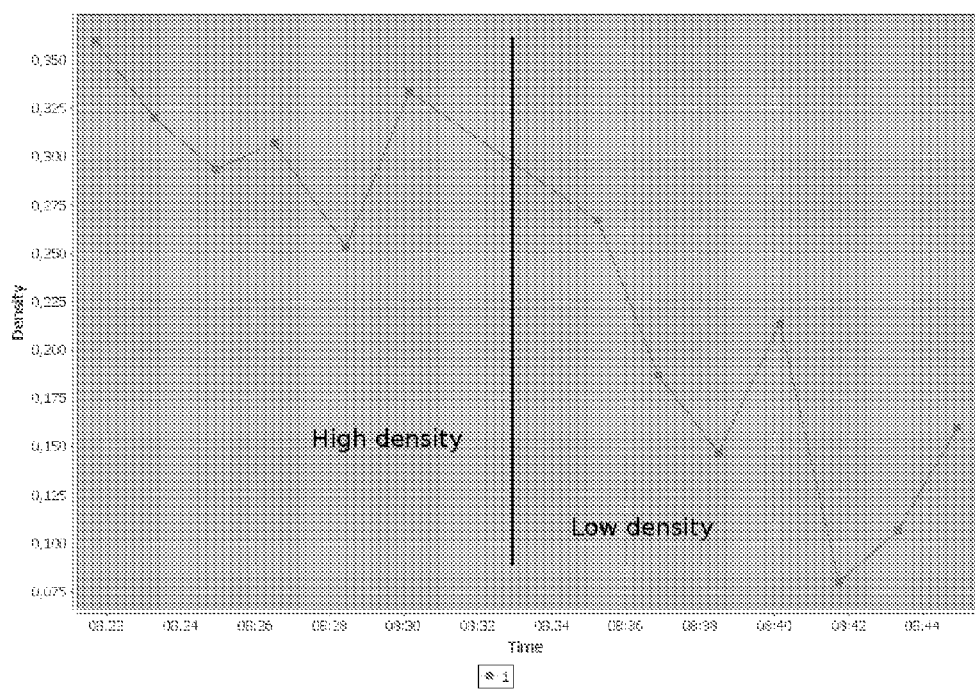
FIG. 6 shows an example of use of the counter according to an embodiment of the invention for counting *Acartia tonsa*, where density of copepods is shown as a function of time.

An example of a density count at given times is provided in FIG. 6, where an image is acquired at approximately every second minute. The number of individual copepods was counted per image in the test, and the density of copepods estimated. Copepod density is plotted as a function of time. The numbers for copepod density in FIG. 6 are uncalibrated numbers, but the relative variations between the numbers are correct. Calibration of the counter may be performed by comparing with manual counts of copepods. The perpendicular line indicates the time at which the density of copepods was reduced. The number of copepods counted by the counter, and thus the estimated copepod density, follows the reduction of density.

Figure 7:
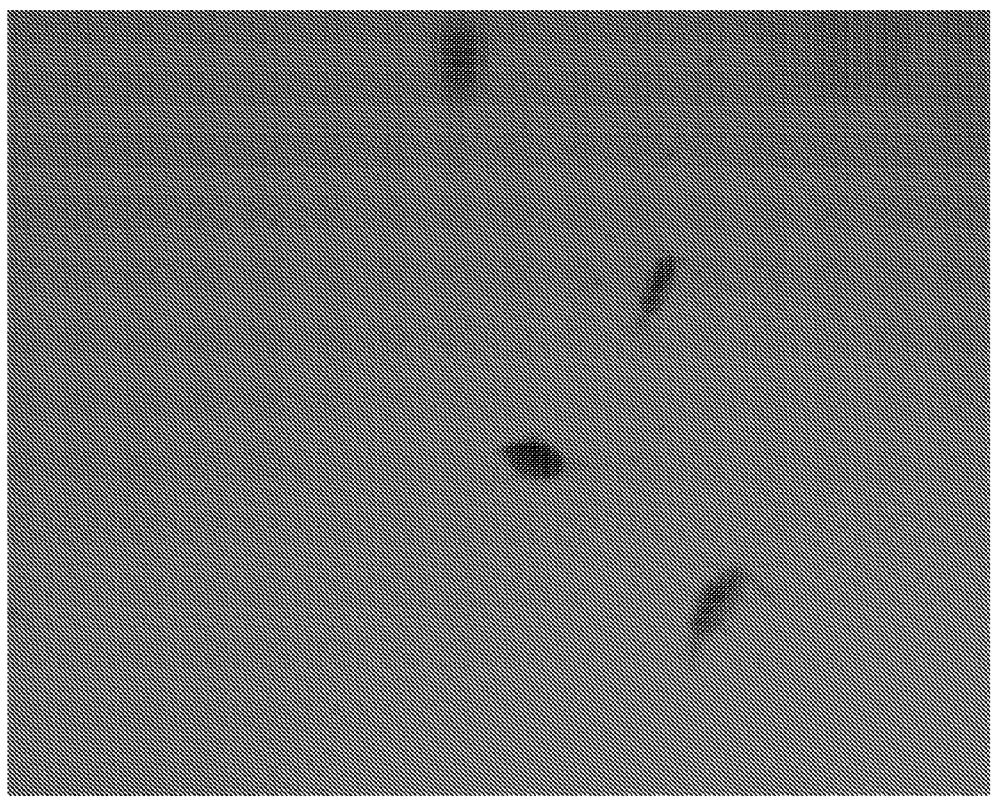
FIG. 7 shows an example of the use of the counter according to an embodiment of the invention provided with two light sources, where an image shows a number of individual *Acartia tonsa* in different degrees of focus.

FIG. 7 shows an example where two light emitting diodes were used. The image shows four to five individual copepods in different degree of focus; i.e., some copepods are in focus whereas others are less in focus. Sharpness is determined for each of the four individuals. The individual closest to the center of the image and the one above and to the right of the center are of sufficient sharpness to be counted. The tests show that good contrast is achieved with the use of two light emitting diodes. Preferably, the shutter time of the camera should be as low as possible (approximately 6, 7 ms), providing good sharpness when there is a certain motion of the copepods in the volume to be photographed.

Having described preferred embodiments of the invention, it will be apparent to those skilled in the art that other embodiments incorporating the concepts may be used. These and other examples of the invention illustrated above are intended by way of example only and the actual scope of the invention is to be determined from the following claims.

The invention claimed is:

1. A method for density measurement of zooplankton in situ in an aqueous solution, the method comprising:
   acquiring at least one image of a volume of the aqueous solution;

processing the at least one image and identifying particles in the at least one image;

analyzing the identified particles based on a sharpness of each particle, and identifying zooplankton to be counted;

wherein analyzing the sharpness of each particle comprises:
- tracing a boundary of each identified particle,
- calculating an intensity gradient for each pixel along the boundary of each particle from the at least one image based on a rate of change of intensity between neighboring pixels,
- calculating a mean intensity gradient of all the pixels along the boundary of each particle, and
- correcting the mean intensity gradient for a general contrast level in the at least one image.

2. The method according to claim 1, further comprising filtering the identified particles in the at least one image based on shape parameters identifying which particles are zooplankton to be counted.

3. The method according to claim 1, further comprising controlling an illumination device for illumination of the volume of the aqueous solution in interaction with image acquiring and processing.

4. Use of the method according to claim 1 for establishing a density of zooplankton in an aqueous solution.

5. Use of the method according to claim 1 for controlling a distribution of food to zooplankton in an automated copepod egg production facility.

6. A non-transitory computer-readable medium having a computer program stored thereon, the computer program being adapted to be executed in a computer comprising a processor, and the computer program causing the computer to perform the method according to claim 1.

7. A non-transitory computer program product having stored thereon instructions for performing the method according to claim 1.

8. A system for density measurement of zooplankton in situ in an aqueous solution, comprising:
- an imaging device for acquiring at least one image of a volume of the aqueous solution;
- and
- an image processing device performing image processing of the at least one image from the imaging device identifying particles in the at least one image, analyzing the identified particles based on a sharpness of each particle, and identifying zooplankton to be counted;

wherein analyzing the sharpness of each particle comprises:
- tracing a boundary of each identified particle,
- calculating an intensity gradient for each pixel along the boundary of each particle from the at least one image based on a rate of change of intensity between neighboring pixels,
- calculating a mean intensity gradient of all the pixels along the boundary of each particle, and
- correcting the mean intensity gradient for a general contrast level in the at least one image.

9. The system according to claim 8, wherein the imaging device comprises a camera housing including at least one digital camera.

10. The system according to claim 8, further comprising at least one illuminating device illuminating the volume of the aqueous solution.

11. The system according to claim 10, further comprising a controller controlling the imaging device and the at least one illuminating device based on feedback from the image processing device.

12. Use of the system according to claim 8 for establishing a density of zooplankton copepods in an aqueous solution.

13. Use according to claim 12, wherein the zooplankton are copepods.

14. Use of the system according to claim 8 for controlling a distribution of food to copepods in an automated zooplankton egg production facility.

15. The system according to claim 8, further comprising a plate arranged at a distance from the imaging device, the distance and a view angle of the imaging device defining the volume of the aqueous solution imaged by the imaging device.

* * * * *